United States Patent [19]

Opie et al.

[11] Patent Number: 4,852,551

[45] Date of Patent: Aug. 1, 1989

[54] CONTAMINATION-FREE ENDOSCOPE VALVES FOR USE WITH A DISPOSABLE ENDOSCOPE SHEATH

[75] Inventors: Eric A. Opie, Brier; Fred E. Silverstein, Seattle, both of Wash.

[73] Assignee: Opielab, Inc., Seattle, Wash.

[21] Appl. No.: 185,115

[22] Filed: Apr. 22, 1988

[51] Int. Cl.⁴ .............................................. A61B 1/00
[52] U.S. Cl. ....................................... 128/4; 137/595; 137/863; 604/34
[58] Field of Search ................... 128/4, 6; 604/33, 34, 604/902; 251/4, 7; 137/863

[56] References Cited

U.S. PATENT DOCUMENTS

| 4,519,385 | 5/1985 | Atkinson et al. | 604/902 X |
| 4,524,802 | 6/1985 | Lawrence et al. | 137/595 |
| 4,537,209 | 8/1985 | Sasa | 128/4 X |
| 4,646,722 | 3/1987 | Silverstein et al. | 128/4 |

FOREIGN PATENT DOCUMENTS 775476 5/1957 United Kingdom ................... 251/7

Primary Examiner—William H. Grieb
Attorney, Agent, or Firm—Seed & Berry

[57] ABSTRACT

An endoscope and valve system specially adapted for use with a disposable sheath having a plurality of channels and respective resilient tubes extending therefrom. In one embodiment, the resilient tubes extend along grooves formed in the side of an endoscope control handle and are captured behind a pivotably mounted access door. The valve system pinches the tubes against the door. The pinching mechanism selectively releases the tubes by pressing respective valve-actuating buttons on the control handle. In another embodiment, the tubes are placed in external pinch valves which are selectively actuated by actuating switches mounted on the control handle.

28 Claims, 4 Drawing Sheets

SUCTION CLOSED

SUCTION OPEN

SUCTION CLOSED

SUCTION OPEN

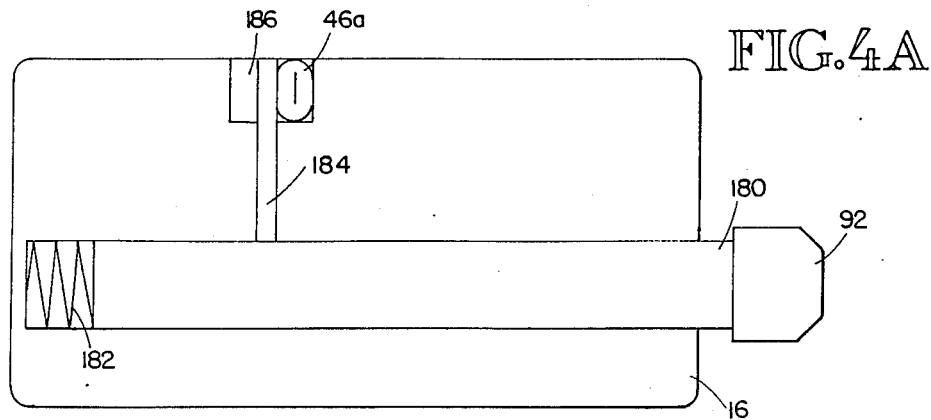
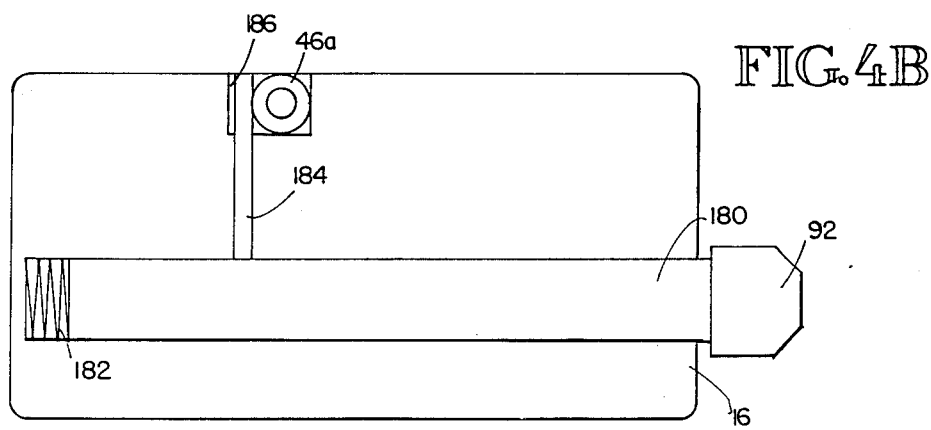
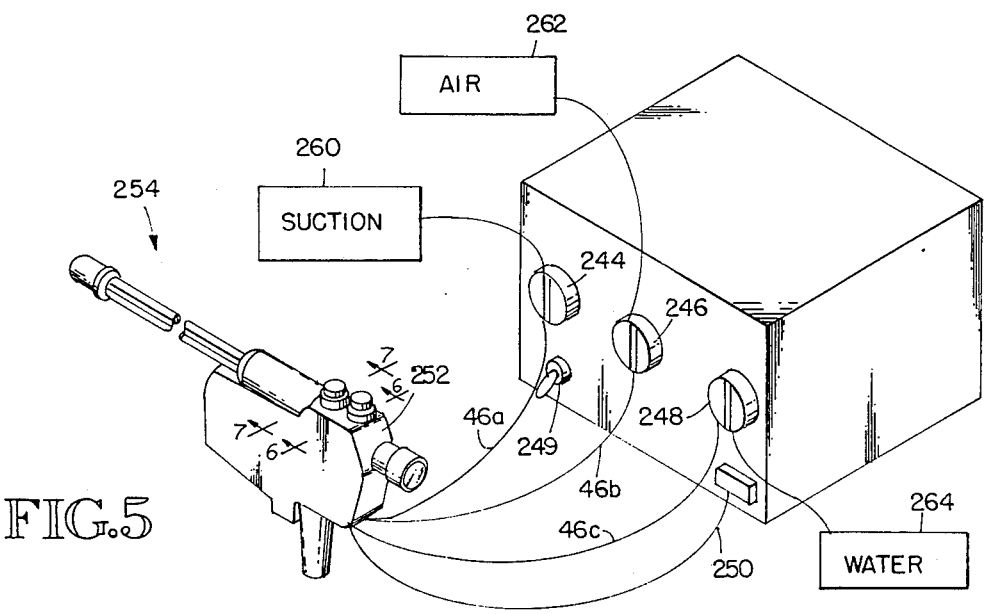

CONTAMINATION-FREE ENDOSCOPE VALVES FOR USE WITH A DISPOSABLE ENDOSCOPE SHEATH

DESCRIPTION

TECHNICAL FIELD

This invention relates to the field of endoscopy, and more particularly, to contamination-free air, water and suction valves of an endoscope used with a disposable endoscope sheath having air, water and suction channels.

BACKGROUND ART

The use of endoscopes for diagnostic and therapeutic indications is rapidly expanding. To improve performance, endoscopes have been optimized to best accomplish their purpose. Therefore, there are upper endoscopes for examination of the esophagus, stomach and duodenum; colonoscopes for examining the colon; angioscopes for examining blood vessels; bronchoscopes for examining the bronchi; laparoscopes for examining the peritoneal cavity; and arthroscopes for examining joint spaces. The discussion which follows will apply to all of these types of endoscopes.

Instruments to examine the rectum and sigmoid colon, known as "flexible sigmoidoscopes," are good examples of the usefulness of endoscopic technology. These devices are expensive, and they are used in a contaminated environment for a procedure which is brief (five to ten minutes) and where problems of cleaning time and contamination are important factors. There has been a large increase in the use of the flexible sigmoidoscope for use in screening symptomatic and asymptomatic patients for colon and rectal cancer. Ideally, flexible sigmoidoscopes must be used rapidly and inexpensively in order to maintain the cost of such screening at acceptable levels. Typically, a clinic would like to perform five sigmoidoscope examinations each hour. A significant problem with making such examinations quick and inexpensive is the time necessary for adequately cleaning the device.

Although endoscopes can be cleaned in about two to four minutes, this relatively cursory cleaning may not be adequate for complete disinfection or sterilization. Even a more complete cleaning, requiring on the order of eight to ten minutes, may not allow adequate cleaning, particularly in view of the increasing problems with contagious viruses. Even with the use of chemicals such as gluteraldehyde, adequate cleanliness may not be possible.

The cleaning problem not only includes the outside of the endoscope but also the multiple small channels inside the endoscope. This includes channels for: air insufflation; water to wash the tip; and biopsy and suction. Each channel also has a control valve. These channels extend along the length of the endoscope and come into contact with body tissues and fluids. It is extremely difficult to adequately clean these channels even when skilled health practitioners spend a great deal of time on the cleaning procedure.

Even if endoscopes can be adequately cleaned in eight to ten minutes, the cleaning still prevents endoscopy examinations from being relatively inexpensive. While a physician may spend five to ten minutes performing some types of endoscopy, he or she will generally waste a great deal of time waiting for the endoscope to be cleaned before he or she can conduct another endoscopy. A partial solution to the "idle time" problem is to purchase multiple instruments so one can be used as the others are being cleaned. However, the expense of having duplicate endoscopes of each of the many types described above makes this solution impractical, especially for physicians' offices and smaller clinics.

Not only must the idle time of the physician be added to the cost of endoscopic examinations, but the time spent by a nurse or other hospital personnel in the cleaning as well as the cost of disinfecting chemicals and other costs of the cleaning process must also be added to the cost of the examination. Although automatic washing machines are available to clean endoscopes, these machines are expensive, take up significant amounts of space, are noisy and are not faster than washing by hand. Further, regardless of whether the cleaning is done manually or by machine, the cleaning chemicals can be harmful to the endoscope and thus significantly shorten its life. The cleaning chemicals, being toxic, are also potentially injurious to the staff who use them and to the environment into which they are discharged. To use some of these chemicals safely, such as gluteraldehyde, requires a dedicated ventilated hood, which uses up space and is expensive to install and operate. The chemicals are also potentially toxic to the patient in that, if residue remains after cleaning and rinsing the instrument, the patient could have a reaction to the chemicals.

As a result of these many problems, conventional endoscope cleaning techniques greatly increase the cost of endoscopic procedures. Furthermore, while the risk of contamination using endoscopes is often far less than the risk of alternative procedures, such as surgery, there is nevertheless a risk that endoscopes are not cleaned adequately to prevent the risk of transmission of infectious diseases from one patient to the next.

In the health care field, the problems of contaminated instruments transmitting disease from one patient to the next have generally been solved by making such instruments disposable. However, this approach has not been thought possible in the field of endoscopy because endoscopes are very expensive instruments. Moreover, it has not been thought possible to isolate the endoscope from the patient or the external environment because the endoscope itself has channels inside it that are used as a conduit for body fluids and tissues, such as, for example, in taking biopsies. The only method currently available to actually sterilize an endoscope is to use gas sterilization with ethylene oxide gas. However, there are several disadvantages in using this procedure. The procedure is very slow (up to 24 hours), during which time the endoscope cannot be used. Also, the gas affects the plastic of the endoscope and may limit its lifespan. Finally, the gas is toxic, and, therefore, great care must be taken to ensure that no residue remains that might cause patient or staff irritation or allergic reaction during contact with the endoscope.

As a result of the above-described limitations in using and cleaning endoscopes by conventional techniques, there has not heretofore been an acceptable solution to the problem of making endoscopy procedures both inexpensive and entirely safe.

A new approach to the problem of endoscope contamination is described in U.S. Pat. No. 4,646,722. This new approach involves the use of an endoscope sheath having a flexible tube surrounding the elongated core of an endoscope. The flexible tube has a transparent window near its distal end positioned in front of the viewing window of the endoscope. Channels that come into contact with the patient or the patient's body fluids (e.g., channels for taking biopsies, injecting air or injecting water to wash the window of the sheath) extend along the endoscope, either inside or outside the sheath. Where the channels are positioned inside the sheath, they may be inserted in a longitudinal groove formed in the endoscope core. The protective sheath may be used with either end-viewing endoscopes or side-viewing endoscopes. The protective sheath may be installed by rolling the elastomeric tube or casing into an annular configuration and then unrolling the tube over the core of the endoscope. Alternatively, the tube may be inflated in its unrolled configuration to expand the tube and allow it to be easily slipped onto the endoscope core. A variety of specialized endoscopes may be created by using protective sheaths having a variety of special purpose medical instruments mounted at the end of a biopsy channel and operated through the channel.

After use of the endoscope, the sheath and channel insert are removed and disposed of, leaving the endoscope free of contamination resulting from the endoscopic procedure. An essential aspect of this approach is incorporating the channels into the system so that the flow of air or liquids through the channels can be controlled without spreading contamination. These channels are essential for many types of endoscopy. In gastroenterology, the channels are used for insufflation of air to open the otherwise closed lumen of the intestinal organs, for spraying water over the tip lens to clean off obscuring mucus, stool or blood, and for suctioning fluid, blood or mucus which is obscuring the examination. The suction channel is the same channel used in most designs for passage of a variety of instruments for diagnosis (biopsy forceps, brushes for cytology, etc.) and therapy (snares to remove polyps, probes to stop ulcer bleeding, etc.).

All of the above-described channels are contaminated in the course of an endoscopy. In the currently used endoscopes (fiberoptic and video), these channels and their valves are the most difficult portions of the endoscope to clean. The suction channel is grossly contaminated with secretions including blood, mucus and stool in every case. A valve in continuity with the inside of the channel is also instantly contaminated. The air and water channels present slightly different problems. The direction of the flow of the air and water is towards the end of the endoscope. Therefore, one might think that these channels could not become contaminated. In fact, however, because of capillary action as well as gravity, both of these small channels are always contaminated with secretions during endoscopy, including blood, stool and mucus. Further, the small size of these channels makes them very hard to clean. If any residue remains, the residue can react with gluteraldehyde, which is commonly used to clean the channels, to produce a thick substance that can plug the channel. This plug is very difficult to remove and sometimes requires that the endoscope be returned to the manufacturer for replacement of the channel. Each of the channels (air and water) also has a valve control which is in continuity with the channel and is potentially contaminated during endoscopy.

The disposable endoscope sheath described in U.S. Pat. No. 4,646,722, which is incorporated herein by reference, reduces the contamination caused by these channels and their valves. With this protective sheath, the air, water and suction channels are entirely disposable. However, it is essential to be able to control flow through these channels to be able to perform endoscopy. Therefore, it is necessary to be able to control the flow of air or liquid through these channels yet be able to dispose of all contaminated components after the procedure. It is therefore important that the valve mechanism controlling the flow of air or liquid through the channels not touch the inside of the channel. As a result, contamination of the valves cannot occur.

An additional requirement for a valve system for the channels is that the valve be located between the contaminated distal area of the tube and the pump portion (for air and water channels) so that contamination cannot get back past the valve to the source of the air and water. For the suction channel, the system incorporates a suction trap (which is routinely used with current endoscopes). The direction of flow of the suction is towards the trap. With the disposal of contaminated tubing and the use of a clean trap for each patient, contamination of the next patient is not possible.

A final requirement of a valve system for the endoscope channels is that it be easily used by endoscopists. Thus, the valve system must allow accurate control of air, water and suction. Furthermore, it should be actuated by essentially the same type of control motions with which endoscopists have become familiar. Ideally, the valve system should have the same "feel" as conventional endoscope valve systems so that the endoscopist will scarcely be aware that he or she is using a specially designed valve system.

DISCLOSURE OF THE INVENTION

It is the object of the invention to provide a valve system for an endoscope used with a disposable sheath having disposable air, water and suction channels.

It is another object of the invention to provide an endoscope valve system for use with a disposable sheath that does not contact the interior of the channels and thus cannot become contaminated.

It is another object of the invention to provide an endoscope valve system for use with a disposable sheath that is installed between the contaminated portions of the channels and uncontaminated sources of air and water.

It is still another object of the invention to provide an endoscope valve system for use with a disposable sheath that operates in the same manner and with the same "feel" as conventional endoscope valve systems.

It is a further object of the invention to provide an endoscope valve system for use with a disposable sheath in which disposable channels may be easily and quickly installed, thereby minimizing the downtime of the endoscope.

These and other objects of the invention are provided by an endoscope for use with a disposable sheath having a casing, a plurality of channels associated with the casing, and a plurality of resilient tubes extending from respective channels. The control handle of the endoscope includes manually actuated valve means having a plurality of valve-actuating members mounted therein. The valve means selectively pinch off the tubes responsive to actuation of a respective valve-actuating member to control the flow of fluid through the tubes without allowing any contact between the interiors of the tubes and the valve means or control handle. In a first embodiment, the control handle includes an access door movable between an open position, in which the tubes can be placed behind the access door, and a closed position in which the tubes are positioned between the access door and a portion of the control handle on which the access door is mounted. The valve means then pinches the tubes against the access door. In the first embodiment, the valve-actuating member for at least one of the tubes includes a linear cam slidably received in the control handle and movable along its longitudinal axis between outer and inner positions. A cam follower extending perpendicularly from the cam toward the access door compresses the tube against the access door when the cam is in its outer position and allows the tube to open when the cam is actuated to its inner position. In the first embodiment, the valve means for at least two of the tubes preferably includes a linear cam slidably received in the control handle and movable between an outer position and first and second inner positions. A first cam follower extends perpendicularly from the cam toward the access door to compress one of the tubes against the access door when the cam is in its outer position in order to allow the tube to open when the cam is actuated to its first inner position and to once again compress the tube when the cam is in its second inner position. A second cam follower extending perpendicularly from the cam toward said access door compresses the other tube against the access door when the cam is in its outer position and when it is in its first inner position, and allows the tube to open when the cam is actuated to its second inner position.

In a second embodiment, the valve means includes an electrically operated pinch valve for each of the tubes. The pinch valves pinch the tubes closed until the valves are actuated by a respective actuation signal. The valve-actuating members comprise actuating rods slidably mounted in the control handle of the endoscope. The actuating rods project outwardly from the control handle and they are resiliently biased toward their outer positions. The valve means further includes a switch for each of the pinch valves. The switches are coupled to the actuating rods to produce the actuating signals when the actuating rods are pressed into the control handle.

BRIEF DESCRIPTION OF THE DRAWINGS

FIGS. 4A and 4B are cross-sectional views of another embodiment of a valve for pinching resilient tubes in an endoscope control handle.

FIG. 5 is a cross-sectional view showing the structure and mode of operation of an alternative embodiment of a suction valve.

FIG. 7 is a cross-sectional view showing the structure and mode of switches for controlling air and water valves in the embodiment of FIG. 5.

BEST MODE FOR CARRYING OUT THE INVENTION

Figure 1:
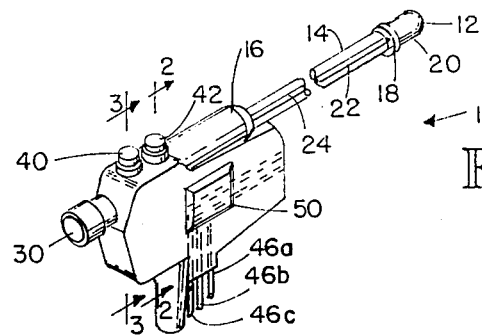
FIG. 1 is an isometric view of the control handle of an endoscope employing one embodiment of the inventive valve system.

As illustrated in FIG. 1, the inventive endoscope 10, like conventional endoscopes, includes a tip portion 12, a flexible insertion tube 14, and a control handle 16. However, the inventive endoscope 10 is adapted for use with a disposable sheath 18 having a protective outer casing 20 terminating in a window (not shown) and one or more channels 22 that are adapted to fit into a groove 24 formed in the insertion tube 14 of the endoscope. The tip portion 12 includes an optics window (not shown) located behind the window of the sheath 18. The optics window of the endoscope is positioned in front of an imaging system (not shown) and an illumination system (not shown). The imaging system may be either video or fiberoptic, i.e., either a miniature television camera or a set of aligned optical fibers. The illumination system may be either electrical or fiberoptic, i.e., an electrically powered light or an optical fiber that receives light externally. The imaging system also includes wires extending through the insertion tube 14 for communicating with a television camera and supplying power to a light if a video imaging system is used or, alternatively, optical fibers extending through the insertion tube 14 and terminating at the optics window 20 if a fiberoptic imaging system is used. The insertion tube 14 also contains control cables (not shown) extending between the control handle 16 and the tip portion 12. As explained below, the control cables bend the tip portion 12 as desired to point the optics window 20 in the desired direction.

As mentioned above, the sheath 18 includes one or more channels 22. These channels typically include a suction channel, an air channel, and a water channel that extends to a nozzle (not shown) for cleaning the optics window of the sheath.

The control handle 16 performs several functions. In the event that a fiberoptic imaging system is used, the optical fiber terminates at an eyepiece 30 through which the clinician can view an image of the tissue in front of the optics window at the tip portion 12 of the endoscope 10. The control handle 16 also includes a connector for connecting an illuminating optical fiber to a light source to communicate the illumination to the optical window in the tip portion 12. If a video imaging system is used, the control handle 16 includes an electrical connector (not shown) for applying a video signal to a monitor and for powering the light behind the optics window in the tip portion 12.

The control handle 16 also includes a manually actuatable valve 40 for the suction channel and a single, manually actuatable valve 42 for both the water and air channels. The use of one valve 40 to control the suction channel 22a and one valve 42 to control both the air and water channel 22b, 22c is the same arrangement used in conventional endoscopes. Also, like conventional endoscopes, the valves 40, 42 of the inventive endoscope 10 are actuated by pressing respective valve-actuating buttons in the control handle 16.

The control handle 16 also includes several control wheels that control the bending of the tip portion 12. Each of the control wheels retracts one control cable while extending an opposite control cable. The control cables extend through the insertion tube 14 and terminate in the tip portion 12. The control cables are arranged so that retracting one cable while allowing another cable to extend bends the tip portion 12 in the direction of the retracted cable. The inventive endoscope 10, like conventional endoscopes, include two control wheels. One control wheel bends the tip portion 12 up and down while the other control wheel bends the tip portion 12 right and left.

In a conventional endoscope, the operating mechanism of the suction, air and water valves communicates with the interiors of the suction, air and water channels, respectively. As a result, the valves become contaminated, and this contamination is difficult to remove. In the inventive endoscope 10, the operating mechanisms of the suction valve 40 and the air/water valve 42 do not come into contact with the interiors of the suction channel and the air and water channels. As a result, the valves 40, 42 do not become contaminated and they need not be cleaned.

The valves 40, 42 are able to avoid any contact with the interiors of the channels 22 because they operate by pinching tubes 46 communicating with the channels 22 until the lumens of the tubes 46 collapse. The tubes 46 communicating with the channels 22 extend along one side of the control handle 16 in respective grooves 48 beneath a pivotably mounted access door 50. The access door is locked shut with a conventional latching mechanism 52 during use, but it may be opened to place the tubes 46 beneath the door 50. As explained in greater detail below, the tubes 46 are selectively compressed against the access door 50 to pinch off the tubes 46.

The access door 50 performs an important role in preventing contamination of the tubes 46 because it allows the control handle 16 to surround the tubes 46 without threading the ends of the tubes 46 through an aperture or passage in the control handle 16. If the tubes 46 could not be placed into the control handle 16 from the side, it would be necessary to thread the ends of the tubes 46 through a valve mechanism. However, when a contaminated tube 46 is removed from the valve mechanism, contaminated fluids from inside the tubes 46 could spill out the ends of the tubes 46 onto the valve mechanism. This contamination could then be transferred to a clean tube as it was being threaded through the valve mechanism. The use of an access door 50 to place the tubes 46 in contact with the valve mechanism allows the tubes 46 to be installed and removed without the ends of the tubes 46 ever coming into contact with the valve mechanism.

The suction valve 40 and the air/water valve 42 utilize similar mechanisms. The suction valve, as illustrated in FIG. 2, includes a linear cam 60 that is slidably mounted in the control handle 16. The cam 60 has an actuating button 62 mounted on its outer end, and its inner end is biased outwardly by a coil return spring 64 of conventional design. The cam 60 has formed therein a first sloped cam surface 66, a second sloped cam surface 68, and a flat cam surface 70 positioned therebetween. A cylindrical cam follower 72 is rotatably mounted on the inner end of a keyed actuator pin 74. The outer end of the actuator pin 74 is formed into a dull knife edge 76 that makes contact with the suction tube 46a. The wall of the suction tube 46a is resilient so that it inwardly biases the actuator pin 74. A spring (not shown) could also be used to resiliently bias the actuator pin 74.

The valve 40 may also include a second cylindrical cam follower 80 rotatably mounted on the inner end of a keyed pin 82. Pin 82 is biased inwardly by a conventional coil spring 84. As explained in greater detail below, the elastic properties of the coil spring 84 are selected to match the elastic properties of the suction tube 46a.

Figure 2A:
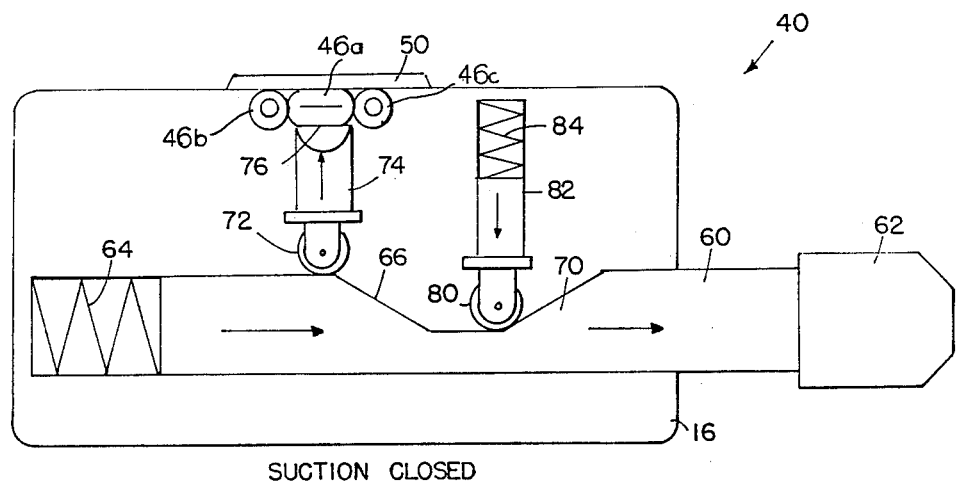
FIGS. 2A and 2B are cross-sectional views taken along the line 2—2 of FIG. 1 showing the structure and mode of operation of a suction valve.

The suction valve 40 is shown in its unactuated position in FIG. 2A in which the suction tube 46a is closed. When the valve 40 is in its unactuated position, the cam follower 72 contacts the outer surface of the cam 60 so that the pin 74 compresses the suction tube 46a against the access door 50. With the cam 60 in this position, the lumen of the suction tube 46a is pinched shut and the cam follower 80 mounted on pin 82 rests against the flat inner cam surface 70.

Figure 2B:
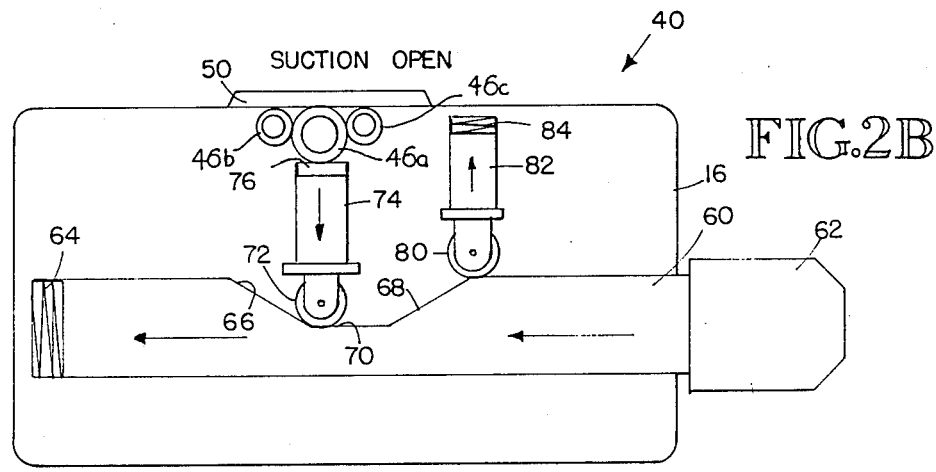

When the endoscopist wants to suction fluid through the suction channel 22a of the sheath 18, he or she presses the actuating button 62 inwardly to the position illustrated in FIG. 2B. The cam follower 72 then rolls down the sloped cam surface 66, thereby allowing the resiliency of the suction tube 46a to push the pin 74 inwardly and open the lumen of the suction tube 46a. A suction is then applied to the suction channel 22a of the sheath 18. When suction is to be terminated, the endoscopist releases the actuating button 62, thereby allowing the return spring 64 to slide the cam 60 outwardly. The cam follower 72 then rolls upwardly along the sloped cam surface 66, thereby displacing the pin 74 outwardly to pinch off the suction tube 46a.

The spacing between the cam followers 72 and 80 is selected so that, when the cam follower 72 is rolling inwardly along the sloped cam surface 66, the cam follower 80 is rolling outwardly along the sloped cam surface 68. Conversely, when the cam follower 72 is rolling outwardly along the sloped cam surface 66, the cam follower 80 is rolling inwardly along the sloped cam surface 68. The slopes of the cam surfaces 66, 68 are preferably the same, so that, if the elastic characteristics of the spring 84 are chosen to match the elastic characteristics of the suction tube 46a, the elastic force of the tube 46a will be exactly compensated by the elastic force of the spring 84. If a matching spring 84 cannot be found for a particular tubing 46a, then the spring 84, in conjunction with cam slope 68, can be fabricated to match the tubing's elastic forces. Under these circumstances, the force characteristics of the cam 60 will be determined entirely by the elastic properties of the return spring 64. The return spring 64 preferably has a linear force characteristic so that the "feel" of the suction valve 40 will match the feel of the suction valves of conventional endoscopes. Thus, although the second cam follower 80 and pin 82 are not essential, they do allow the suction valve 40 of the inventive endoscope 10 to operate with the same response characteristics as conventional endoscopes.

Figure 3A:
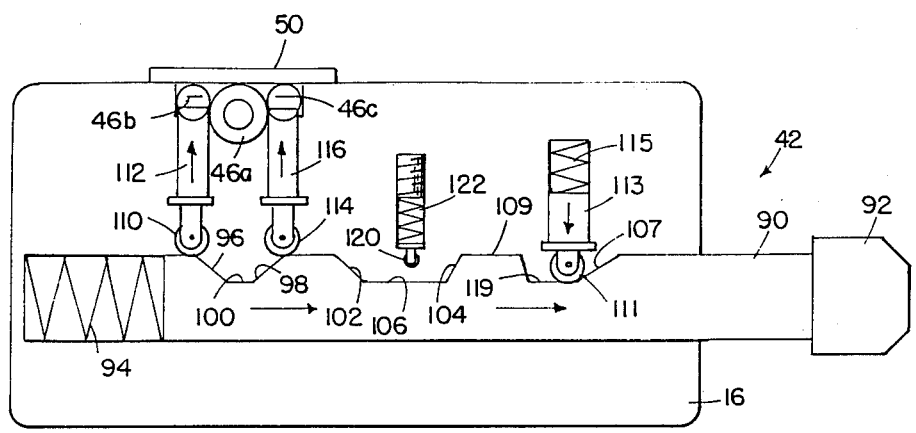
FIGS. 3A, 3B and 3C are cross-sectional views taken along the line 3—3 of FIG. 1 showing the structure and mode of operation of a combination air and water valve.
Figure 3B:
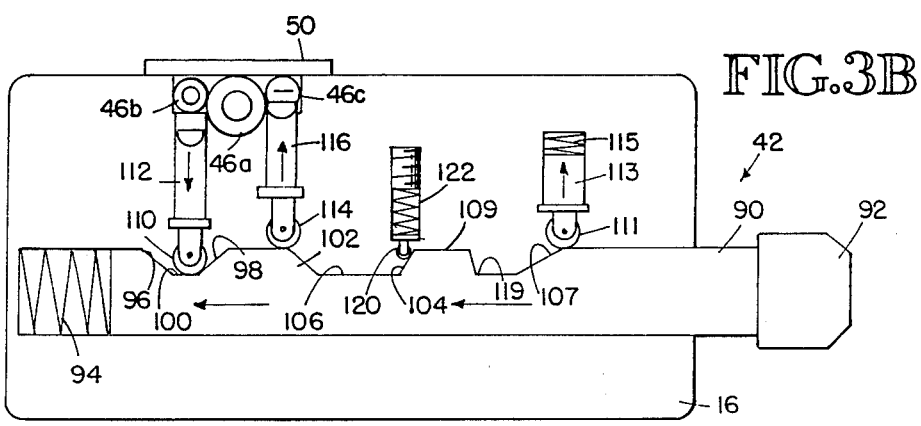

The structure and mode of operation of the air/water valve 42 are illustrated in FIG. 3. Like the suction valve 40, the air/water valve 42 utilizes a linear cam 90 slidably mounted in the control handle 16. Also, an actuating button 92 is mounted on the outer end of the cam 90, while the inner end is outwardly biased by a coil return spring 94 of conventional design. The cam includes a first pair of sloped cam surfaces 96, 98 separated by a flat cam surface 100, a second pair of sloped cam surfaces 102, 104 that are also separated by a flat cam surface 106, and a third sloped cam surface 107. The cam surfaces 96–100 contact a first cylindrical cam follower 110 that is rotatably mounted at the inner end of a keyed actuator pin 112. The outer end of the actuator pin 112 is formed into a dull knife edge that contacts the air tube 46b beneath the access door 50. Similarly, the cam surfaces 102–106 contact a second cylindrical cam follower 114 that is rotatably mounted at the inner end of a second keyed actuator pin 116. The outer end of the actuator pin 116 is formed into a dull knife edge that contacts the water tube 46c beneath the access door 50. The cam surface 104 also contacts a cam follower 120 mounted at the end of a spring 122 when the actuating button 92 has been pressed to open the air tube 46b, as illustrated in FIG. 3B. The cam follower 120 and spring 122 serve as a detent to provide tactile feedback when the linear cam 90 has been actuated a sufficient distance to open the air tube 46b. Further actuation of the cam 90 lifts the cam follower 120 onto cam surface 109 and allows the linear cam 90 to be actuated further to open the water tube 46c, as explained in greater detail below.

The cam surface 107 contacts a cylindrical cam follower 111 that is rotatably mounted on the lower end of a keyed pin 113. The pin 113 is biased toward the cam 90 by a coil string 115. As explained below, the cam follower 110, pin 113 and spring 115, along with the cam surface 107, balance the closing forces for pin 112 so that the return spring 94 need not generate the entire force necessary to close the air tube 46b.

The air/water valve 42 is shown in FIG. 3A in its unactuated position. In this position, the cam followers 110, 114 both contact outer surfaces of the cam 90, thereby forcing their respective valve pins 112, 116 outwardly so that they pinch closed the air tube 46b and water tube 46c. The detent cam follower 120 free floats over the flat inner cam surface 106 in this unenergized position, and the compensating cam follower 111 rests on flat cam surface 119.

When the endoscopist wants to inject air into the organ being examined, the actuator button 92 is pressed to force the cam 90 inwardly to the position shown in FIG. 3B. In this position, the cam follower 120 contacts the sloping cam surface 104, thereby providing a resistance to further inward movement of the cam 90. The cam follower 120 and surface 104 thus provide tactile feedback to the endoscopist that the valve 42 has been actuated to open the air tube 46b. The spacing between the cam followers 110, 111 and the sloped cam surfaces 96, 107 are selected so that the cam follower 111 rolls up the sloped cam surface 107 when the cam follower 110 rolls down the sloped cam surface 96. As a result, assuming that the elastic properties of the spring 115 are properly selected, the force that must be exerted on the cam 90 to force the pin 112 outwardly against the air tube 46b is compensated for by the force exerted by the cam follower 111 on the sloped cam surface 107 of the cam 90. The inward force that must be exerted on the actuator button 92 is thus determined solely by the elastic properties of the return spring 94. Like the return spring 64 for the suction valve 40 (FIG. 2), the return spring 94 preferably has a linear force characteristic so that the "feel" of the suction valve 42 will match the feel of the air/water valves of conventional endoscopes. Thus, although the cam follower 111 and spring 115 are not essential, they do allow the air/water valve 42 to operate with the same response characteristics as conventional endoscopes.

Figure 3C:
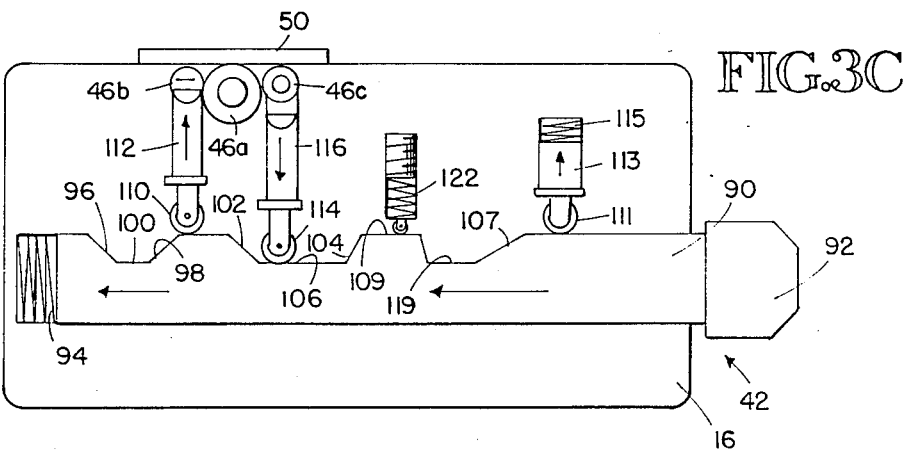

When the endoscopist wants to clean the window of the sheath 18 with water flowing through the water channel 22c, the cam is pressed all the way in to the position illustrated in FIG. 3C. In this position, the cam follower 110 has rolled up the sloped cam surface 98 so that the pin 112 is once again pinching off the air tube 46b. At the same time, the cam follower 114 rolls down the sloped cam surface 102, thereby allowing the resiliency of the water tube 46c to push the pin 116 inwardly and open the water tube 46c. The cam surfaces 110, 102 have the same slope, and the air and water tubes 46b, c have the same elastic properties. As a result, the force that must be exerted on the cam 90 to force the pin 112 outwardly against the air tube 46b is compensated for by the force that the cam follower 116 exerts on the sloped cam surface 102. When the cam 90 is moving between the positions shown in FIGS. 3B and C, the cam follower 111 remains on a flat surface 121 of the cam 90 so that it has no effect on the inward forces that must be exerted on the actuating button 92. The inward force that must be exerted on the actuator button 92 is thus determined solely by the elastic properties of the return spring 94.

The valve system makes it virtually impossible for contamination to flow up the air or water tubes 46b, 46c past the valves 40, 42 to the air and water sources. Either the tubes 46b, 46c are clamped shut or air and water are flowing through them in the direction of the tip portion 12 of the endoscope. The valves 40, 42 do not actually touch any of the contaminated fluid and, therefore, they cannot contaminate a tube that is subsequently placed in that position.

At the conclusion of the procedure, all of the tubes 46, including the channels 22 in the sheath 18, the portions of the tubes 46 extending along the side of the control handle 16 and the portions of the tubes 46 extending to the air and water sources, are discarded. The entire suction tube 46a is, of course, contaminated during an endoscopy. This tube 46a, as with the air and water tubes 46b, 46c, is completely removed after the endoscopic procedure is completed. For the next patient, the tube 46a is replaced and a clean fluid trap is placed in the circuit at the suction device. There is no chance for contamination to pass from the suction source and fluid trap to the patient through a new suction tube 46a and suction channel 22a because the suction tube 46a either is closed by the valve 40 or is under suction in the direction moving from the tip portion 12 of the endoscope 10 proximally to the suction device. The portion of the suction tube 46a used to pass endoscope accessories (from the endoscope sheath proximal portion to the distal portion at the endoscope tip portion 12) is entirely replaced after each patient and, therefore, is no longer a potential source of patient-to-patient contamination. It should be noted that the cam followers 72, 80, 110, 114, 111 need not be rotatably mounted but could be sliding surfaces on respective cams.

Another embodiment of the endoscope valves is illustrated in FIG. 4. In this embodiment, the actuating button 92 is mounted at the end of an actuating rod 180 that is resiliently biased in an outer direction by a coil spring 182. The actuating rod 180 is slidably mounted in the control handle 16. A pinch member 184 projects upwardly into a groove 186 containing the biopsy tube 46a. As illustrated in FIG. 4A, in its unactuated position, the actuating rod 180 is biased outwardly 182 so that the pinch member 184 pinches the biopsy tube 46a closed. When the actuating button 92 is pressed, the actuating rod 180 slides further into the handle 16 so that the actuating member 184 allows the lumen of the biopsy tube 46a to open and allow suction through the biopsy tube 46a. In the embodiment of FIG. 4, an access door 50 (FIGS. 2 and 3) is not required since the biopsy tube 46a is pinched against the wall of the groove 186. The actuating button 92 must, of course, be actuated to place the biopsy tube 46a in the groove 186.

Figure 6:
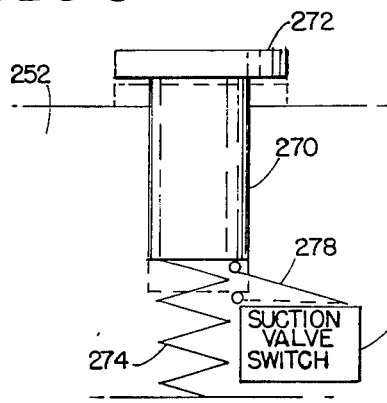
FIG. 6 is an isometric view of an another embodiment of the inventive valve system utilizing an electromechanical approach.

The endoscope valve system illustrated in FIGS. 1-3 is entirely mechanical. An electromechanical system can also be used, as illustrated in FIGS. 5-7. With reference to FIG. 5, an electromechanical system 240 utilizes a control module 242 having three conventional pinch valves 244, 246, 248 receiving the suction, air and water tubes 46a, 46b, 46c, respectively. Each of the tubes 46 is inserted into a respective slotted opening so that the ends of the tubes 46 never come into contact with the pinch valves 244-248. Until the valves 244-248 are actuated, they pinch the tubes 46 shut. A switch 249 on the control module 242 may be actuated to open the pinch valves 244-248 in order to allow the tubes 46 to be inserted through the slots into the valves 244-248. The valves 244-248 are actuated through a control line 250 extending from a specially configured control handle 252 of an endoscope 254 to a connector 256 on the control module 242. As explained in greater detail below, the valves 244-248 normally pinch the respective tubes 46 closed, but they are actuated to open the tubes 46 when a respective electrical switch in the control handle 252 is closed. Respective tubes 46a, 46b, 46c extend from the control module 242 to a conventional suction device 260, a conventional source of compressed air 262, and a conventional source of pressurized water 264.

The structure and mode of operation of the switch for the suction valve 244 are illustrated in FIG. 6. An actuating rod 270 having an actuating button 272 on its outer end is slidably received in the control handle 252. The actuating rod 270 is biased outwardly by a coil spring 274. A conventional microswitch 276 having a switch lever 278 is mounted in the control handle 252 beneath the actuating rod 270, with the switch lever 278 contacting the inner end of the rod 270. When the rod 270 is in its outer position, the switch lever 278 is allowed to extend outwardly away from the switch 276, thereby opening the switch 276. When the rod 270 is pressed in, the rod 270 displaces the switch lever 278, thereby closing the switch 276 and causing the pinch valve 244 to open the suction tube 46a so that the suction device 260 can apply a suction to the suction channel 22a of the sheath 18.

The control for the air and water valves 246, 248, respectively, is more complex since they are both operated from the same actuating rod so that the endoscope 254 will operate in the same manner as a conventional endoscope. With reference to FIG. 7, an inner actuating rod 290 having an actuating button 292 on its outer end is slidably received in an outer actuating rod 294 having an actuating button 296 on its outer end. The outer actuating rod 294 is, in turn, slidably received in the control handle 252. A cylindrical actuating cam 298 is formed on the inner end of the inner actuating rod 290. The inner actuating rod 290 is biased outwardly by a coil spring 300, while the outer actuating rod 294 is biased outwardly by a coil spring 302 extending between its end and the cam 298 on the inner actuating rod 290. The spring 300 has a spring constant that is higher than that of the spring 302 so that the rods 290, 294 remain in the position illustrated in FIG. 7A until they are actuated. A first conventional microswitch 310 having a switch lever 312 is mounted in the control handle 252, with the switch lever 312 contacting the inner end of the outer actuating rod 294. A second conventional microswitch 316 having an switch lever 318 is mounted in the control handle 252 with the switch lever 318 positioned just beneath the cam 306. The first switch 310 controls the operation of the water valve 248 (FIG. 5), while the second switch 316 controls the operation of the air valve 246.

In operation, when the endoscopist wants to inject air into the organ being examined, he or she presses the actuating button 292, thereby displacing the inner rod 290 inwardly until the cam 298 pushes the actuating lever 318 of the switch 316 outwardly, as illustrated in FIG. 6B. The movement of the actuating lever 318 closes the switch 316, thereby actuating the air valve 246 on the control module 242 to allow air to flow through the air tube 46b and the air channel 22b of the sheath 18. Note that the outer actuating rod 294 remains in its original position so that the water valve 248 remains closed.

Figure 7C:
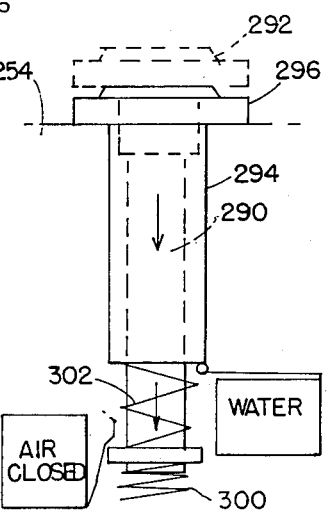
FIGS. 7A, 7B and 7C are cross-sectional views showing the structure and mode of a switch for controlling a suction valve in the embodiment of FIG. 5.
Figure 7A:
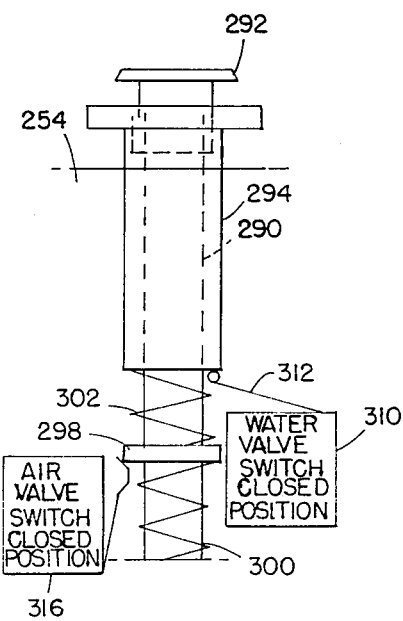
Figure 7B:
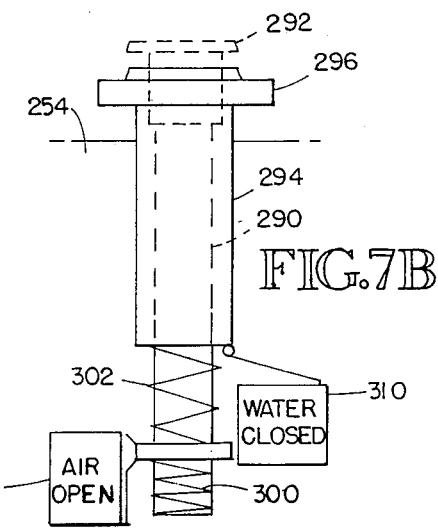

With reference now to FIG. 7C, pressing both the inner actuating button 292 and the outer actuating button causes both the inner actuating rod 290 and the outer actuating rod 294 to move inwardly. This further inward movement of the inner actuating rod 290 causes the cam 298 to clear the actuating lever 318 of the air switch 316 so that the switch 316 returns to its original open condition. Inward movement of the outer actuating rod 294 displaces the switch lever 312, thereby closing the switch 310 and causing the pinch valve 248 to open the water tube 46c so that the water supplying device 264 can supply water to the water channel 22c of the sheath 18.

The system 240 of FIGS. 5-7 makes it impossible to have contamination between patients for several reasons. First, all of the tubes 46 extending from the tip portion 12 of the endoscope to the sources are discarded after use. Second, the pinch valves 244-248 close each tube 46 before the tubes 46 reach the source. No contaminated portion of the tubes 46 or other components touches the pinch valves 244-248. Therefore, when the tubes 46 and channels 22 of the sheath are replaced, the new tubes 46 can again be pinched by the valves without any contamination. Either the air and water tubes 46b, 46c are pinched off or fluid is flowing in them in the direction of the endoscope tip portion 12. It is thus not possible for contamination to get far up the tubes 46 because of these two possible states of activation. Although the suction tube 46a is contaminated during an endoscopy, it is removed after the endoscopic procedure is completed. For the next patient, the tube 46a is replaced and a clean fluid trap is placed in the circuit at the suction device. There is no chance for contamination to pass from the suction source and fluid trap to the patient through a new suction tube 46a and suction channel 22a because the suction tube 46a either is closed by the valve 244 or is under suction in the direction moving from the tip portion 12 of the endoscope 10 proximally to the suction device. The portion of the suction tube 46a used to pass endoscope accessories (from the endoscope sheath proximal portion to the distal portion at the endoscope tip portion 12) is replaced after each patient and, therefore, is no longer a potential source of patient-to-patient contamination. As a result, at the conclusion of the procedure when the tubes 46 and sheath 18 are replaced, the system is left entirely clean.

The above design was configured to mimic as near as possible endoscopes currently in use. A simpler system could use a single shaft with a detent system to selectively activate the switches. The system could work much the same as the air, water and suction valves of the mechanical system with the cam followers replaced by switches. The timing of the cams would need to be optimized for switch operation also.

We claim:

1. An endoscope for use with a disposable sheath having a casing, a plurality of channels associated with said casing and a plurality of resilient tubes extending from respective channels, said endoscope comprising:
   a flexible insertion tube having distal and proximal ends;
   a tip portion formed at the distal end of said insertion tube, said insertion tube and tip portion being surrounded by the casing of said sheath when said sheath is installed on said endoscope;
   a control handle secured to said insertion tube at the proximal end thereof; and
   manually actuated valve means having a plurality of valve-actuating members mounted in said control handle, said valve means selectively pinching off said tubes responsive to actuation of a respective valve-actuating member to control the flow of fluid through said tubes without allowing any contact between the interiors of said tubes and said valve means or control handle.

2. The endoscope of claim 1 wherein said control handle includes an opening adapted to capture said tubes without threading the ends of said tubes through said control handle and wherein said valve means pinches off said tubes within said control handle.

3. The endoscope of claim 2 wherein said control handle includes an access door movable between an open position, in which said tubes may be placed behind said access door, and a closed position in which said tubes are positioned between said access door and a portion of said control handle on which said access door is mounted, and wherein said valve means applies a pinching force to said tubes toward said access door, whereby said tubes are pinched between said valve means and said access door.

4. The endoscope of claim 3, further including a plurality of grooves running along an outer surface of said control handle and intersecting said access door, said grooves being adapted to receive said tubes therein in order to releasably secure said tubes to said control handle and guide said tubes to said access door.

5. The endoscope of claim 2 wherein said valve-actuating member for at least one of said tubes includes a linear cam slidably received in said control handle and movable along its longitudinal axis between outer and inner positions, said cam having inner and outer cam surfaces, with said outer cam surface being positioned radially outward from said inner cam surface, and wherein said valve means include a return spring resiliently biasing said cam toward its outer position, and a cam follower extending perpendicularly from the longitudinal axis of said cam toward said access door, said cam follower contacting said outer cam surface and compressing said tube against said access door when said cam is in its outer position, and said cam follower contacting said inner cam surface to allow said tube to open when said cam is actuated to its inner position.

6. The endoscope of claim 5 wherein a first sloping cam surface extends from said outer cam surface to said inner cam surface and wherein said valve means further includes a second sloping cam surface extending from a second outer cam surface to a second inner cam surface, said valve means further including a second cam follower resiliently biased against said cam by a compensating spring, said second cam follower being positioned so that said second cam follower moves along said second sloping cam surface from said second inner cam surface to said second outer cam surface as said first cam follower moves along said first sloping cam surface from said first outer cam surface to said first inner cam surface, the slope of said second sloping cam surface and the elastic properties of said compensating spring being chosen so that the force that said second cam follower exerts on said cam along its longitudinal axis counteracts the force that said first cam follower exerts on said cam along its longitudingal axis as said cam is actuated between its inner and outer positions, whereby the force required to actuate said cam from its outer to its inner position is determined primarily by said return spring.

7. The endoscope of claim 2 wherein said valve means for at least two of said tubes comprise:
   a linear cam slidably received in said control handle and movable along its longitudinal axis between an outer position and first and second inner positions, said cam having first and second outer cam surfaces separated by a first inner cam surface and third and fourth outer cam surfaces separated by a second inner cam surface, said outer cam surfaces being positioned radially outward from said inner cam surfaces;
   a return spring resiliently biasing said cam toward its outer position;
   a first cam follower extending perpendicularly from the longitudinal axis of said cam toward said access door, said cam follower contacting said first outer cam surface and compressing one of said tubes against said access door when said cam is in its outer position, said cam follower contacting said first inner cam surface to allow said tube to open when said cam is actuated to its first inner position, and said cam follower contacting said second outer cam surface and compressing said tube against said access door when said cam is in its second inner position; and
   a second cam follower extending perpendicularly from the longitudinal axis of said cam toward said access door, said cam follower contacting said third outer cam surface and compressing the other of said tubes against said access door when said cam is in its outer position, said cam follower contacting said fourth outer cam surface and compressing said tube against said access door when said cam is actuated to its first inner position, and said cam follower contacting said second inner cam surface to allow said tube to open when said cam is actuated to its second inner position, whereby inward movement of said cam to its first and second inner positions sequentially opens respective tubes.

8. The endoscope of claim 7, further including detent means for providing tactile feedback as said cam is actuated between its first and second inner positions.

9. The endoscope of claim 7 wherein a first sloping cam surface extends between said first inner cam surface and said second outer cam surface and wherein a second sloping cam surface extends between said fourth outer cam surface and said second inner cam surface, said second cam follower being positioned so that said second cam follower moves along said second sloping cam surface from said fourth outer cam surface to said second inner cam surface as said first cam follower moves along said first sloping cam surface from said first inner cam surface to said second outer cam surface, the slopes of said first and second sloping cam surfaces being identical so that the force that said second cam follower exerts on said cam along its longitudinal axis counteracts the force that said first cam follower exerts on said cam along its longitudinal axis as said cam is actuated between its first and second inner positions, whereby the force required to actuate said cam from its first inner position to its second inner position is determined primarily by said return spring.

10. The endoscope of claim 9 wherein a third sloping cam surface extends from said first outer cam surface to said first inner cam surface and wherein said valve means further includes a fourth sloping cam surface extending from a third inner cam surface to a fifth outer cam surface, said valve means further including a third cam follower resiliently biased against said cam by a compensating spring, said third cam follower being positioned so that said third cam follower moves along said fifth sloping cam surface from said third inner cam surface to said fifth outer cam surface as said first cam follower moves along said third sloping cam surface from said first outer cam surface to said first inner cam surface, the slope of said third sloping ca surface and the elastic properties of said compensating spring being chosen so that the force that said third cam follower exerts on said cam along its longitudinal axis counteracts the force that said first cam follower exerts on said cam along its longitudinal axis as said cam is actuated from its outer position to its first inner position, whereby the force required to actuate said cam from its outer position to its first inner position is determined primarily by said return spring.

11. The endoscope of claim 10 wherein a detent surface is positioned between said third sloping cam surface and said fifth outer cam surface to provide tactile feedback as said cam is actuated between its first and second inner positions.

12. The endoscope of claim 7 wherein said second and third outer cam surfaces coincide with each other.

13. The endoscope of claim 1 wherein in at least one groove is formed in said handle to receive a respective resilient tube, and wherein said valve means comprise:
an actuating rod slidably mounted in said control handle and projecting outwardly therefrom, said rod having a clamping member projecting therefrom into said groove adjacent said tube; and
means for resiliently biasing said actuating rod toward its outer position so that said clamping member pinches said resilient tube against a wall of said groove, whereby inward actuation of said actuating rod releases said clamping member from said resilient tube to open the lumen of said tube.

14. The endoscope of claim 1 wherein said valve means includes an electrically operated pinch valve for each of said tubes, said pinch valves pinching said tubes closed until said valves are actuated by a respective actuation signal, and wherein said valve-actuating members comprise actuating rods slidably mounted in said control handle and projecting outwardly therefrom, said actuating rods being resiliently biased toward their outer positions, said valve means further including a switch for each of said pinch valves, said switches being coupled to said actuating rods to produce said actuating signals when said actuating rods are pressed into said control handle.

15. The endoscope of claim 14 wherein said valve means for two of said tubes comprise an outer actuating rod slidably mounted in said control handle and an inner actuating rod slidably mounted in said outer actuating rod so that said inner and outer rods are coaxially arranged, said actuating rods being resiliently biased outwardly from said control handle, with said inner actuating rod projecting outwardly beyond the end of said outer actuating rod, said valve means further including a first switch operatively coupled to said inner actuating rod and being actuated only when said inner actuating rod has been pressed into said control handle so that the outwardly projecting end of said inner actuating rod is approximately flush with the outwardly projecting end of said outer actuating rod, and a second switch operatively coupled to said outer actuating rod and being actuated only when said outer rod has been pressed into said control handle a predetermined distance, whereby the pinch valve connected to said first switch can be actuated by pressing said inner rod until its end is flush with said outer rod, and the pinch valve connected to said second switch can be actuated at the same time that the pinch valve connected to said first switch is deactivated by pressing both of said actuating rods into said control handle.

16. The endoscope of claim 1 wherein said control handle further includes a plurality of grooves extending along its outer surface to receive respective resilient tubes of said casing to guide said tubes to said valve means.

17. The endoscope of claim 1 wherein said valve means includes an electrically operated pinch valves for each said tubes, said pinch valves being positioned externally from said handle to pinch the respective tubes closed until said valves are actuated by a respective actuating signal, and wherein said valve-actuating members comprise respective switches mounted in said control handle; said switches communicating with respective of said electrically operated pinch valves to produce said actuating signals when said switches are manipulated on said control handle thereby allowing fluid to flow through said tubes.

18. In a control valve handle for an endoscope specially adapted for use with a disposable sheath having a plurality of channels and a plurality of resilient tubes extending from respective channels, a valve system for controlling the flow of fluids through said tubes, said valve system comprising manually actuated valve means having a plurality of valve-actuating members mounted in said control handle, said valve means selectively pinching off said tubes responsive to actuation of a respective valve-actuating member to control the flow of fluid through said tubes without allowing any contact between the interiors of said tubes and said valve means or control handle, said control handle further including an access door movable between an open position, allowing said tubes to be placed behind said access door, and a closed position in which said tubes are positioned between said access door and a portion of said control handle on which said access door is mounted, and wherein said valve means applies a pinching force to said tubes toward said access door, whereby said tubes are pinched between said valve means and said access door.

19. In a control valve handle for an endoscope specially adapted for use with a disposable sheath having a plurality of channels and a plurality of resilient tubes extending from respective channels, a valve system for controlling the flow of fluids through said tubes, said valve system comprising manually actuated valve means having a plurality of valve-actuating members mounted in said control handle, said valve means selectively pinching off said tubes responsive to actuation of a respective valve-actuating member to control the flow of fluid through said tubs without allowing any contact between the interiors of said tubes and said valve means or control handle, said control handle, the valve-actuating member for at least one of said tubes including a linear cam slidably received in said control handle and movable along its longitudinal axis between outer and inner positions, said cam having inner and outer cam surfaces, with said outer cam surface being positioned radially outward from said inner cam surface, and wherein said valve means include a return spring resiliently biasing said cam toward its outer position and a cam follower extending perpendicularly from the longitudinal axis of said cam toward said access door, said cam follower contacting said outer cam and compressing said tube against said access door when said cam is in its outer position, and said cam follower contacting said inner cam surface to allow said tube to open when said cam is actuated to its inner position.

20. The valve system of claim 19 wherein a first sloping cam surface extends from said outer cam surface to said inner cam surface and wherein said valve means further includes a second sloping cam surface extending from a second outer cam surface to a second inner cam surface, said valve means further including a second cam follower resiliently biased against said cam by a compensating spring, said second cam follower being positioned so that said second cam follower moves along said second sloping cam surface from said second inner cam surface to said second outer cam surface as said first cam follower moves along said first sloping cam surface from said first outer cam surface to said first inner cam surface, the slope of said second sloping cam surface and the elastic properties of said compensating spring being chosen so that the force that said second cam follower exerts on said cam along its longitudinal axis couteracts the force that said first cam follower exerts on said cam along its longitudinal axis as said cam is actuated between its inner and outer positions, whereby the force required to actuate said cam from its outer to its inner position is determined primarily by said return spring.

21. In a control valve handle for an endoscope specially adapted for use with a disposable sheath having a plurality of channels and a plurality of resilient tubes extending from respective channels, a valve system for controlling the flow of fluids through at least two of said tubes, said valve system comprising:
a linear cam slidably received in said control handle and movable along its longitudinalaxis between an outer position and first and second inner positions, said cam having first and second outer cam surfaces separated by a first inner cam surface and third and fourth outer cam surfaces separated by a second inner cam surface, said outer cam surfaces being positioned radially outward from said inner cam surfaces;
a return spring resiliently biasing said cam toward its outer position;
a first cam follower extending perpendicularly from the longitudinal axis of said cam toward said access door, said cam follower contacting said first outer cam surface and compressing one of said tubes against said access door when said cam is in its outer position, said cam follower contacting said first inner cam surface to allow said tube to open when said cam is actuated to its first inner position, and said cam follower contacting said second outer cam surface and compressing said tube against said access door when said cam is in its second position; and
a second cam follower extending perpendicularly from the longitudinal axis of said cam toward said access door, said cam follower contacting said third outer cam surface and compressing the other of said tubes against said access door when said cam is in its outer position, said cam follower contacting said fourth outer cam surface and compressing said tube against said access door when said cam is actuated to its first inner position, and said cam follower contacting said second inner cam surface to allow said tube to open when said cam is actuated to its second inner position, whereby inward movement of said cam to its first and second inner positions sequentially opens respective tubes.

22. The valve system of claim 21, further including detent means for providing tactile feedback as said cam is actuated between its first and second inner positions.

23. The valve system of claim 21 wherein a first sloping cam surface extends between said first inner cam surface and said second outer cam surface and wherein a second sloping cam surface extends between said fourth outer cam surface and said second inner cam surface, said second cam follower being positioned so that said second cam follower moves along said second sloping cam surface from said fourth outer cam surface to said second inner cam surface as said first cam follower moves along said first sloping cam surface from said first inner cam surface to said second outer cam surface, the slopes of said first and second sloping cam surfaces being identical so that the force that said second cam follower exerts on said cam along its longitudinal axis counteracts the force that said first cam follower exerts on said cam along its longitudinal axis as said cam is actuated between its first and second inner positions, whereby the force required to actuate said cam from its first inner position to its second inner position is determined primarily by said return spring.

24. The valve system of claim 23 wherein a third sloping cam surface extends from said first outer cam surface to said first inner cam surface and wherein said valve means further includes a fourth sloping cam surface extending from a third inner cam surface to a fifth outer cam surface, said valve means further including a third cam follower resiliently biased against said cam by a compensating spring, said third cam follower being positioned so that said third cam follower moves along said fifth sloping cam surface from said third inner cam surface to said fifth outer cam surface as said first cam follower moves along said third sloping cam surface from said first outer cam surface to said first inner cam surface, the slope of said third sloping cam surface and the elastic properties of said compensating spring being chosen so that the force that said third cam follower exerts on said cam along its longitudinal axis counteracts the force that said first cam follower exerts on said cam along its longitudinal axis as said cam is actuated from its outer position to its first inner position, whereby the force required to actuate said cam from its outer position to its first inner position is determined primarily by said return spring.

25. The valve system of claim 24 wherein a detent surface is positioned between said third sloping cam surface and said fifth outer cam surface to provide tactile feedback as said cam is actuated between its first and second inner positions.

26. In a control valve handle for an endoscope specially adapted for use with a disposable sheath having a plurality of channels and a plurality of resilient tubes extending from respective channels, said handle having at least one groove formed in said handle to receive a respective resilient tube, a valve system for controlling the flow of fluids through said tubes, said valve system comprising manually actuated valve means having a plurality of valve-actuating members mounted in said-control handle, said valve means selectively pinching off said tubes responsive to actuation of a respective valve-actuating member to control the flow of fluid through said tubes without allowing any contact between the interiors of said tubes and said valve means or control handle, said control handle further including:
   an actuating rod slidably mounted in said control handle and projecting outwardly therefrom, said rod having a clamping member projecting therefrom into said groove adjacent said tube; and
   means for resiliently biasing said actuating rod toward its outer position so that said clamping member pinches said resilient tube against a wall of said groove, whereby inward actuation of said actuating rod releases said clamping member from said resilient tube to open the lumen of said tube.

27. A method of controlling the flow of fluids through a plurality of tubes connected to respective channels of a disposable endoscope sheath, said method comprising placing said tubes into the control handle of an endoscope without threading the ends of said tubes through said control handle and selectively pinching off said tubes within said control handle.

28. A method of controlling the flow of fluids through a plurality of tubes connected to respective channels of a disposable endoscope sheath mounted in an insertion tube extending from a handle of an endoscope said method comprising;
   providing said handle with a plurality of switches corresponding in number to the number of said tubes;
   placing said tubes into respective electrically operated pinch valves without threading the ends of said tubes through said pinch valves; and
   selectively actuating said switches on said handle to engage respective pinch valves to selectively control the pinching off of said tubes.

* * * * *

UNITED STATES PATENT AND TRADEMARK OFFICE
CERTIFICATE OF CORRECTION

PATENT NO. : 4,852,551

DATED : August 1, 1989

INVENTOR(S) : Eric A. Opie; Fred E. Silverstein

It is certified that error appears in the above-identified patent and that said Letters Patent is hereby corrected as shown below:

In claim 10, column 15, line 26, delete "ca" and substitute therefor --cam--.

In claim 19, column 17, line 7, delete "tubs" and substitute therefor --tubes--.

In claim 20, column 17, line 42, delete "couteracts" and substitute therefor --counteracts--.

In claim 21, column 17, line 55, delete "longitudinalaxis" and substitute therefor --longitudinal axis--.

Signed and Sealed this

Twelfth Day of June, 1990

Attest:

HARRY F. MANBECK, JR.

Attesting Officer  Commissioner of Patents and Trademarks